(12) United States Patent
Faulkner et al.

(10) Patent No.: US 8,145,644 B2
(45) Date of Patent: Mar. 27, 2012

(54) SYSTEMS AND METHODS FOR PROVIDING ACCESS TO MEDICAL INFORMATION

(75) Inventors: Scott Douglas Faulkner, Newaygo, MI (US); Gary Edward Higbie, Atlanta, GA (US)

(73) Assignee: Interfix, LLC, Newaygo, MI (US)

( * ) Notice: Subject to any disclaimer, the term of this patent is extended or adjusted under 35 U.S.C. 154(b) by 451 days.

(21) Appl. No.: 12/182,759

(22) Filed: Jul. 30, 2008

(65) Prior Publication Data

US 2009/0037474 A1 Feb. 5, 2009

Related U.S. Application Data

(60) Provisional application No. 60/952,936, filed on Jul. 31, 2007.

(51) Int. Cl.
*G06F 17/30* (2006.01)
*G06F 7/00* (2006.01)
(52) U.S. Cl. .......................... 707/748; 707/802
(58) Field of Classification Search ............... 707/748
See application file for complete search history.

(56) References Cited

U.S. PATENT DOCUMENTS

| | | | |
|---|---|---|---|
| 6,970,859 B1* | 11/2005 | Brechner et al. ............... 1/1 |
| 2006/0271401 A1* | 11/2006 | Lassetter et al. ............ 705/2 |
| 2006/0282336 A1* | 12/2006 | Huang .................... 705/26 |
| 2007/0271121 A1* | 11/2007 | Laudan et al. .............. 705/3 |
| 2008/0104116 A1* | 5/2008 | Van Hoe et al. .......... 707/104.1 |

OTHER PUBLICATIONS

Cimino, et al., "Coping with Changing Controlled Vocabularies," 1994, 26 pages.
Cimino, "Integrating Clinical Systems by Integrating Controlled Vocabularies," 1994, 36 pages.
Cimino, "Use of the UMLS in Patient Care," 1994, 15 pages.
Cimino, "Vocabulary for the CPR," 1994, 5 pages.
Chute, et al., "Advanced Patient Information Systems and Medical Concept Representation," Med Info' 95 Workshop, 1995, 33 pages.
Cimino, "Controlled Vocabularies for Capturing Clinical Encounters," 1995, 10 pages.
Cimino, "Medical Informatics Introduction and Overview," 1995, 34 pages.
Cimino, "Medinfo '95 Plennary Talk," 1995.
Cimino, "Overview of Medical Computing," 1995, 14 pages.
Cimino, "The Informatics Superhighway: Prototyping on the World Wide Web," 1995, 2 pages.
Cimino, "The Promise of Pathology Informatics," 1995, 52 pages.
Cimino, et al., "Automated Guidelines Implemented via the World Wide Web," in Gardner RM, ed.: Proceedings of the Nineteenth Annual Symposium on Computer Applications in Medical Care, Oct.-Nov. 1995, 3 pages.

(Continued)

*Primary Examiner* — Kuen Lu
(74) *Attorney, Agent, or Firm* — Kilpatrick Townsend & Stockton LLP

(57) ABSTRACT

Various aspects and embodiments of the present invention relate to providing a medical application with access to medical information from validated medical information experts. The medical information experts can be validated by scoring attributes of a purported medical information expert, generating a rank based on the score, and comparing the score to a pre-set threshold. The medical information from validated medical information experts can be stored in a knowledge database. A request from a medical application can be received and used to search the knowledge database to generate a response to the request that includes part of the medical information. The response can be provided to the medical application in a format that can be customized by the medical application.

20 Claims, 11 Drawing Sheets

OTHER PUBLICATIONS

Cimino, et al., Cognitive Evaluation of a Knowledge-based Vocabulary, Dec. 7-8, 1995, 2 pages.
Socratous, et al., "Access to the Clinical Encounter via the World Wide Web," 1995, 13 pages.
Cimino, "1996 AMIA Annual Fall Symposium," 1996, 24 pages.
Cimino, "Using the Web for Research, Education, and Patient Care: What Works, What's Broken, What Needs to Be Built, The Web as Electronic Medical Record I: Components," 1996, 26 pages.
Cimino, "Web-Based Clinical Information Systems: Architecture, Perils and Promises," 1996, 30 pages.
Cimino, et al., "Building Web Client Interfaces to Legacy Systems," 1996, 6 pages.
Cimino, et al., "From Coded Patient Data to World Wide Web Information via the UMLS," 1996, 26 pages.
Cimino, et al., "Just Tell Me What You Want!: The Promises and Perils of Rapid Prototyping with the World Wide Web," 1996, 20 pages.
Cimino, et al., "Managing Vocabulary for a Centralized Clinical System," 1996, 36 pages. (French language version).
Cimino, et al., "Managing Vocabulary for a Centralized Clinical System: Automated Knowledge-Based Techniques Putting Theory into Practice," 1996, 35 pages (English language version).
Ciminio, "Patient Access to Clinical Information on the Web: PatCIS," 1997, 11 pages.
Cimino, "Access to Health Care Information Resources through Intelligent Controlled Terminologies," 1997, 12 pages.
Cimino, "Access to Information Sources through Controlled Vocabulary," 1997, 13 pages.
Cimino, "Accessing Clinical Information of the Internet and the World Wide Web," 1997, 3 pages.
Cimino, "Desiderata for Controlled Medical Vocabularies in the Twenty-First Century," 1997, 44 pages.
Cimino, "Desirable Clinical Terminology Characteristics and Present Adherence," 1997, 39 pages.
Cimino, "Detection of Ambiguity in the UMLS Metathesaurus," 1997, 6 pages.
Cimino, "Intranet Technology in Hospital Information Systems," 1997, 20 pages.
Cimino, "Terminology to Support Merging Data Sets," 1997, 8 pages.
Cimino, "The Needs for Coding and Classification Systems," 1997, 17 pages.
Cimino, "Web Access to the EMR at Columbia-Presbyterian Medical Center," 1997, 2 pages.
Cimino, et al., "Designing a Student Clinical Workstation: Challenges and Opportunities," 1997, 3 pages.
Cimino, et al., "Supporting Infobuttons with Terminologic Knowledge," 1997, 9 pages.
Cimino, "Bringing the Web to the Bed(side)," 1998, 11 pages.
Cimino, "Desiderata for Controlled Medical Vocabularies," 1998, 46 pages.
Cimino, "Electronic Patient Records at New York Presbyterian Hospital," 1998, 6 pages.
Cimino, "Internet Diagram, Web Browser—Web Server" 1998, 1 page.
Cimino, "Patient Access to Electronic Medical Records," 1998, 11 pages.
Cimino, "Use of the Internet for Database Access," 1998, 32 pages.
Cimino, "Web-Based Medical Records Design and Implementation at Columbia-Presbyterian Medical Center," 1998, 27 pages.
Cimino, et al., "Architecture for a Web-Based Clinical Information System that Keeps the Design Open and the Access Closed," 1998, 36 pages.
Huff, et al., "Development of a Standard Terminology to Support Medication Messages," 1998, 60 pages.
Cimino, "Medical Informatics Training at Columbia University: Perceived Needs for and Goals of Training," 1999, 13 pages.
Cimino, "Attacking the Hard Problems of IAIMS," 1999, 22 pages.
Cimino, "Bringing Clinical Information to the Bedside with the World Wide Web," 1999, 72 pages.
Cimino, "Clinical Vocabularies," 1999, 10 pages.
Cimino, "Controlled Medical Terminologies: What can they do for me?" 1999, 48 pages.
Cimino, "Controlled Terminology in Clinical Practice," 1999, 62 pages.
Cimino, "Cornerstone I: Representing Knowledge—From Data to Knowledge Through Concept-Oriented Terminologies," 1999, 122 pages.
Cimino, "Electronic Reporting," 1999, 3 pages.
Cimino, "HL7 Drug Name Coordination Efforts," 1999, 31 pages.
Cimino, "Integration of Information Resources at the Point of Need," 1999, 49 pages.
Cimino, "National Library of Medicine Training Directors Meeting," Jul. 8-9, 1999, 4 pages.
Cimino, "PatCIS: An Experiment with Patient Access," 1999, 28 pages.
Cimino, "Terminology Tools: State of the Art and Practical Lessons," 1999, 37 pages.
Cimino, et al., "Evaluation of a Proposed Method for Representing Drug Terminology," 1999, 42 pages.
Cimino, et al., "Personal Health Information: The Last Frontier on the World Wide Web," 1999, 55 pages.
Cimino, et al., "What is Wrong with EMR?" 1999, 68 pages.
Cimino, et al., "An Evaluation of Patient Access to their Electronic Medical Records via the World Wide Web," 2000, 23 pages.
Cimino, "Contemporary Issues in Medical Informatics," 2000, 22 pages.
Cimino, "Harnessing World Wide Web Technology and Standardized Terminology to Improve Decision Making for Patients and Providers," 2000, 77 pages.
Cimino, "Information Technology-Based Patient Education for Decreasing Prehospital Delay of Patients Presenting with Acute Myocardial Infarct: The MI-HEART Project," Feb. 17, 2000, 8 pages.
Cimino, "Integrating e-Publishing, Digital Libraries and the Electronic Medical Record," Feb. 4, 2000, 42 pages.
Cimino, "Research Issues Related to the Construction and Use of Advanced Controlled Medical Terminologies," Sep. 12, 2000, 88 pages.
Cimino, "Supporting Medical Decision Making with Electronic Medical Records," 2000, 76 pages.
Cimino, "The Future of NDC: The HL7 Perspective," 2000, 21 pages.
Cimino, "Vision: Impact of Information on the Health Field in the Future," 2000, 7 pages.
Cimino, et al., "The Internet—How Will It Transform the Practice of Medicine?" 2000, 19 pages.
Cimino, "A Systematic Study of the Coordination, Communication and Information Needs for Patient Care in an Academic Health Center," 2001, 28 pages.
Cimino, "Battling Scylla and Charybdis: The Search for Redundancy and Ambiguity in the 2001 UMLS Metathesaurus," 2001, 42 pages.
Cimino, "Delivery of Just-in-Time Information," 2001, 17 pages.
Cimino, "Managing Data for Clinical Care Delivery and Research—Getting More Bang for Your Buck—Standards & Terminologies," 2001, 18 pages.
Cimino, "NCVHS Subcommittee on Standards and Security," 2001, 11 pages.
Cimino, "Palm-Based Extensions to the New York Presbyterian Hospital Clinical Information System: PalmCIS," 2001, 32 pages.
Cimino, "Patients' Access to Medical Records: Experience with PatCIS," 2001, 64 pages.
Cimino, "Technology and the Future of Medicine," 2001, 44 pages.
Cimino, et al., "Web as Medium for Patient Access to Electronic Health Information," 2001, 25 pages.
Cimino, et al., "What do Patients Do with Access to Their Medical Records?" 2001, 27 pages.
Cimino, "Computer-Assisted Decision Making in the Twenty-First Century," 2002, 33 pages.
Cimino, "Intelligent Terminologies to Support System Interfaces: The Medical Entities Dictionary," Apr. 15, 2002, 65 pages.
Cimino, "National Health Information Infrastructure at Columbia University and New York Presbyterian Hospital," 2002, 5 pages.
Cimino, "Panel 3: What Level of Data Granularity, Common Standards, Lexicon Elements, and Definitions Need to be Developed by the Health System Community to Meet the Needs of an Advanced Clinical Information System? Application of Information Technology to the Transformation of Clinical Research and Health Care in the 21st Century," Oct. 30-31, 2002, 14 pages.
Cimino, "Patient Access to Health Information," Jul. 24, 2002, 29 pages.
Cimino, "The Challenge of Reuse of Information," Aug. 27, 2002, 69 pages.
Cimino, "Welcome to MI-HEART," 2002, 14 pages.
Cimino, "Vision: Impact of Information on the Health Field in the Future," 2002, 7 pages.
Cimino, et al., "Theoretical, Empirical and Practical Approaches to Resolving the Unmet Information Needs of Clinical Information System Users," 2002, 26 pages.
Cimino, "Anticipating and Satisfying Clinician Information Needs: The Infobutton Manager Project," Mar. 6, 2003, 72 pages.
Cimino, "Connecting for Health Preliminary Terminology Consensus Statements," May 21, 2003, 25 pages.
Cimino, "PatCIS: An Experiment with Patient Access," 2003, 28 pages.
Cimino, "Selecting a Terminology for HL7 Messages: Evaluation Criteria for External Terminologies," Jan. 16, 2003, 21 pages.
Cimino, "The Columbia University Experience: Infobuttons and the Infobutton Manager," 2003, 10 pages.
Cimino, "The Medical Entities Dictionary," 2003, 27 pages.
Cimino, "The Role of Standard Terminologies in Facilitating Integration," 2003, 27 pages.
Cimino, "Nursing Interventions and Outcomes in Three Older Populations Effectiveness Study," Feb. 10-11, 2003, 55 pages.
Cimino, et al., "Integrating Health Information Resources with Web-Based Clinical Information Systems," 2003, 70 pages.
Cimino, et al., "Mobile Information and Coordination for Health Care," 2003, 25 pages.
Cimino, et al., "Use of Online Resources While Using a Clinical Information System," 2003, 27 pages.
Cimino, "Knowledge Representation, Structuring and Ontology Development," Jun. 4-5, 2003, 23 pages.
Hripcsak, et al., "Clinical Computing and the Repository," 2003, 37 pages.
Cimino, "Infobuttons and Cancer Center Protocols," May 17, 2004, 32 pages.
Cimino, "Just in Time Education: Linking Clinical and Educational Systems," May 19, 2004, 75 pages.
Cimino, "Medical Informatics," May 13, 2004, 55 pages.
Cimino, "Understanding Clinician Information Needs," 2004, 5 pages.
Cimino, et al., "Practical Considerations for Exploiting the World Wide Web to Create Infobuttons," 2004, 26 pages.
Cimino, "Experience with Using the UMLS Semantic Network to Coordinate Controlled Terminologies for a Large Clinical Data Repository," Apr. 8, 2005, 42 pages.
Cimino, "New Desiderata for Biomedical Terminologies," 2005, 19 pages.
Cimino, "Palm-Based Wireless Computing to Improve Access to Health Information and Coordination of Care," Jul. 7, 2005, 47 pages.
Cimino, "Resolving Clinicians' On-Line Information Needs: A Brief History of Buttons," Mar. 24, 2005, 114 pages.
Cimino, "Resolving Clinicians' On-Line Information Needs: A Brief History of Buttons," Jun. 24, 2005, 83 pages.
Cimino, "Resolving Clinicians On-Line Information Needs: A Short History of Buttons," Apr. 11, 2005, 115 pages.
Cimino, "Secondary Uses of Clinical Data," 2005, 23 pages.
Cimino, "Software Certification for Electronic Health Records: The Certification Commission for Healthcare Information Technology (CCHIT)," 2005, 17 pages.
Cimino, "The Columbia University/New York Presbyterian Hospital Medical Entities Dictionary (The MED)," Oct. 14, 2005, 34 pages.
Cimino, "Twenty Years of IAIMS: The Columbia University/New York Presbyterian Hospital Clinical Data Repository," Apr. 10, 2005, 44 pages.
Cimino, "US Standards for Health Record Systems," 2005, 24 pages.
Del Fiol, et al., "Integration of Health Information Resources into Electronic Health Records," 2005, 87 pages.
Cimino, et al., "Using Patient Data to Retrieve Health Knowledge," Oct. 25, 2005, 28 pages.
Cimino, "An Integrated Approach to Computer-Based Decision Support at the Point of Care," 2006, 38 pages.
Cimino, "Personalized Prediction and Resolution of Clinician Information Needs," 2006, 89 pages.
Cimino, "Technical Aspects of the Infobutton Manager," 2006, 57 pages.
Cimino, "Use, Usability, Usefulness and Impact of an Infobutton Manager," 2006, 45 pages.
Cimino, et al., "Integration of Health Information Resources into Electronic Health Records," 2005, 77 pages.
Cimino, "Controlled Terminologies in Patient Care and Research: An Informatics Perspective," 2007, 64 pages.
Cimino, "Determining the Quality of a Terminology," 2007, 35 pages.
Cimino, "Infobuttons: Linking Clinical Information Systems to On-Line Information Resources to Resolve Clinician Information Needs," 2007, 93 pages.
Cimino, "Reuse of Data Coded with High-Quality Terminologies: Practical Examples from Patient Care Settings," 2007, 53 pages.
Cimino, et al., "Medication Reconciliation Using Natural Language Processing and Controlled Terminologies," 2007, 25 pages.
Cimino, et al., "Redesign of the Columbia University Infobutton Manager," 2007, 51 pages.
Del Fiol, et al., "Integration of Health Information Resources into Electronic Health Records Using HL7," 2007, 30 pages.
Gutnik, et al., "Infobuttons: A Study of Usability," 2007, 1 page.
Cimino, "Computer-Based Support for Improving Patient Medication Management," May 16, 2008, 97 pages.
Cimino, "Infobuttons: Anticipatory Passive Decision Support," 2008, 83 pages.
Cimino, "Informatics as an Education Tool: The Future is Now," 2008, 154 pages.
Cimino, "Lessons from Biomedical Informatics for Nutrition Informatics," 2008, 19 pages.
Cimino, "The Biomedical Translational Research Information System (BTRIS)," Jul. 9, 2008, 30 pages.
Cimino, "The Biomedical Translational Research Information System (BTRIS)," Sep. 12, 2008, 74 pages.
Cimino, "The Challenges of Bridging HIS/EMRs and Research Information Systems," 2008, 36 pages.
Cimino, "The Librarian Infobutton Tailoring Environment (LITE)," 2008, 93 pages.
Cimino, "The NIH Biomedical Translational Research Information System (BTRIS)," Feb. 26, 2008, 22 pages.
Cimino, "The NIH Biomedical Translational Research Information System (BTRIS)," Sep. 16, 2008, 17 pages.
Cimino, "Webinar: Publishing for the EHR 101," May 20, 2008, 71 pages.
Cimino, et al. "Leading a Horse to Water: Using Automated Reminders to Increase Use of Online Decision Support," 2008, 28 pages.
McDonald, et al., "Personal Health Records: Past and Future Directions, In Two Acts," 2008, 54 pages.
http://people.dbmi.columbia.edu/~ciminoj/Presentations.html as of Feb. 2009, 4 pp.
http://people.dbmi.columbia.edu/~ciminoj/Publications.html as of Feb. 2009, 5 pp.

* cited by examiner

Reference

| Home | Administration | MT Tools | ahdi AHDI | My Profile | Logout |

Search the Reference Publications mers%

Search requires a minimum of 3 characters.

☐ Click here to view / filter your reference publications

| References | |
|---|---|
| Word | Defined |
| mersalyl (acid) | |
| mersalyl acid | |
| mersalyl exchange assay | |
| mersalyl exchange method | |
| Merseburg triad | |
| Mershon arch | |
| Mershon band pusher | |
| Mersilene band | |
| Mersilene braided nonabsorbable suture | |
| Mersilene fascial strip | |
| Mersilene gauze hammock | |
| Mersilene graft | |
| Mersilene implant | |

☐ Reference Word: mersalyl (acid)

Stedman's Abbreviations, Acronyms & Symbols (3e)
Related Main Entries
MER
Related Sub Entries
MER

Fig. 4B

| Home | Administration | MT Tools | | My Profile |

AHDI Book of Style

T
- t.i.d.
- tables, tabular matter
- tablespoon
- teaspoon
- telephone numbers
- temperature, temperature scales
- tense, verb
- tera-
- that
- that is
- the
- thousand
- time
- time zones
- times symbol (x)
- titles
- TNM staging system for malignant tumors
- tomorrow
- ton g, middle, or end of a word or word string ( %positive% for example will return ng with brex)

AAMT is the recognized leader in acknowledging ractices. This book represents AAMT's most we reached our conclusions through research and n the experience and expertise of a great many students have also had a hand in the creation of ers, supervisors, and originators of dictation to le of persuader, not enforcer. AAMT's conclusions d exactness has established AAMT as the By incorporating our conclusions into your which to justify your decisions and our materials ty or piecemeal, keep in mind that consistency of abbreviation for the United States with or re often reading abbreviated, handwritten notes,

Fig. 5A

| Home | Administration | MT Tools | | My Profile |

AHDI Book of Style                                   ahdi AHDI  508

[temperature, temperature scales] [Lookup] ●

NOTE: You can use the "%" symbol for wildcard searches in the beginning, middle, or end of a word or word string (%positive% for example will return anything with the word positive in it, %brex would return any word ending with brex)

temperature, temperature scales

Express temperature degrees with numerals except for zero.

zero degrees 36 degrees

36°C

Use *minus* (not the symbol) to indicate temperatures below zero.

minus 48°C

If the temperature scale name (Celsius, Fahrenheit, Kelvin) or abbreviation (C, F, K) is not dictated, it is not necessary to insert it.

38°C *or* 38 degrees Celsius *or* 38 degrees

Use the degree symbol (°) if available immediately followed by the abbreviation 500
506

Fig. 5B

AHDI Book of Style

Note: You can use the "%" symbol for wildcard searches (%positive% for example will return anything with the word positive in it)

| Category | Item | Normal Values |
|---|---|---|
| Cardiopulmonary Lab | Cardiac Index | 2.5 - 4.2 L/min/m2 |
| Cytology | Cardiac Output | 4 - 8 LPM |
| General Chemistry | Central Venous Pressure | 2 - 6 mmHg |
| Hematology | Diastolic Arterial Pressure | 60 - 90 mmHg |
| Neurology | Ejection Fraction | 60 – 75% |
| Urology | Left Arterial Pressure | 4 - 12 mmHg |
| Cardiopulmonary Lab | Left Ventricular Stroke Work Index | 40 - 70 g/m2/beat |
| Cardiopulmonary Lab | Mean Arterial Pressure | 70 - 105 mmHg |
| Cardiopulmonary Lab | Pulmonary Artery Diastolic | 5 - 15 mmHg |
| Cardiopulmonary Lab | Pulmonary Artery End Diastolic Pressure | 8 - 10 mmHg |
| Cardiopulmonary Lab | Pulmonary Artery Pressure | 10 - 20 mmHg |
| Cardiopulmonary Lab | Pulmonary Artery Systolic | 15 - 30 mmHg |
| Cardiopulmonary Lab | Pulmonary Artery Wedge Pressure | 4 - 12 mmHg |
| Cardiopulmonary Lab | Pulmonary Vascular Resistance | 155 - 255 dynes/sec/cm-5 |
| Cardiopulmonary Lab | Pulmonary Vaslular Resistance Index | 255 - 285 dynes/sec/cm-5 |

Fig. 6A

AHDI Normal Lab Values

Note: You can use the "%" symbol for wildcard searches (%positive% for example will return anything with the word positive in it)

| Category | Item | Normal Values |
|---|---|---|
| Cardiopulmonary Lab | Cardiac Index | 2.5 - 4.2 L/min/m2 |
| Cardiopulmonary Lab | Cardiac Output | 4 - 8 LPM |
| Cardiopulmonary Lab | Central Venous Pressure | 2 - 6 mmHg |
| Cardiopulmonary Lab | Diastolic Arterial Pressure | 60 - 90 mmHg |
| Cardiopulmonary Lab | Ejection Fraction | 60 – 75% |
| Cardiopulmonary Lab | Left Arterial Pressure | 4 - 12 mmHg |
| Cardiopulmonary Lab | Left Ventricular Stroke Work Index | 40 - 70 g/m2/beat |
| Cardiopulmonary Lab | Mean Arterial Pressure | 70 - 105 mmHg |
| Cardiopulmonary Lab | Pulmonary Artery Diastolic | 5 - 15 mmHg |
| Cardiopulmonary Lab | Pulmonary Artery End Diastolic Pressure | 8 - 10 mmHg |
| Cardiopulmonary Lab | Pulmonary Artery Pressure | 10 - 20 mmHg |
| Cardiopulmonary Lab | Pulmonary Artery Systolic | 15 - 30 mmHg |
| Cardiopulmonary Lab | Pulmonary Artery Wedge Pressure | 4 - 12 mmHg |
| Cardiopulmonary Lab | Pulmonary Vascular Resistance | 155 - 255 dynes/sec/cm-5 |
| Cardiopulmonary Lab | Pulmonary Vascular Resistance Index | 255 - 285 dynes/sec/cm-5 |

Fig. 6B

Physicians

Search 702

NOTE: You can use the "%" symbol for wildcard searches in the beginning, middle, or end of a word or word string (%stien would return Fierstien, Epstien, Rosenstien, etc.)

| First Name | Last Name | Specialty | State | City | Zip Code | |
|---|---|---|---|---|---|---|
| jo | jo | All | All | | | Search |

Results

706

Drag a column header here to group by that column

| First Name | Last Name | City | State | Specialty | Zip Code | Details |
|---|---|---|---|---|---|---|
| John | Joelson | Springfield | MA | Cardiovascular Disease | 01107-1273 | Details |
| John | John | Concord | MA | Neurologist | 01742-4191 | Details |
| Jon | Jolles | Hanover | MA | Pediatrician | 02339-1641 | Details |
| Jo | Johnson | Wells | ME | Ophthalmologist | 04090-4768 | Details |
| John | Johansson | Essex Junction | VT | Sport Medici | | Details |
| John | Joe | New Haven | CT | Otolaryngolo | | Details |
| Jordan | Josephson | New York | NY | Otolaryngolo | | Details |
| John | Joannow | Astoria | NY | Internist | | Details |
| John | Joseph | Forest Hills | NY | Internist | | Details |
| John | Joseph | Rochester | NY | Urologist | | Details |
| John | Johnson | Pittsburgh | PA | Otolaryngolo | | Details |
| Jonas | Johnson | Pittsburgh | PA | Nephrologist | | Details |
| John | Johnson | Pittsburgh | PA | Nephrologist | | Details |
| Joseph | Joseph | Hermitage | PA | Internist | | Details |
| John | Johnson | Altoona | PA | Anesthesiologist | 16601-4804 | Details |

Details — 708

John R Johansson
Company: Champlain Sports Medicine
Specialty: Sport Medicine Specialist
67 Lincoln St
Essex Junction, VT 05452-3235
Phone: 802-878-1003
Fax: 802-878-9961

Copy All To Clipboard

SYSTEMS AND METHODS FOR PROVIDING ACCESS TO MEDICAL INFORMATION

CROSS-REFERENCE TO RELATED APPLICATIONS

This application claims priority to U.S. Provisional Patent Application No. 60/952,936, filed Jul. 31, 2007 and entitled "Systems and Methods for Providing Access to Medical Transcription Information," the entirety of which is hereby incorporated by reference.

FIELD OF THE INVENTION

The present invention generally relates to providing access to medical information that may be used by a computer-implemented medical application.

BACKGROUND

Computer-implemented medical applications can include software programs utilized by medical personnel for performing various tasks and services associated with providing medical services. The medical applications may be used to obtain and/or confirm administrative and substantive information regarding a medical event. Examples of such medical applications include medical coding, electronic health record systems, medical billing systems, speech recognition systems, and medical transcription applications. A medical event may be an office visit by the patient, diagnosis, treatment, medical research, medical topic for classroom instruction or otherwise, or any event associated with a medical area for which administrative and/or substantive information may be needed or confirmed. The medical event may be an office visit by a patient for which a medical provider, such as a doctor, generated notes, medical documentation, or patient instructions.

For example, medical transcription generally involves converting spoken words of a clinician into a text format in electronic form. Examples of content that may be transcribed include notes regarding a patient's visit to the clinician, a hospital or clinic visit, or a recommended or prescribed medication or treatment plan. Typically, medical transcriptionists listen to tapes or voice files containing the clinician's spoken words or acronyms and transcribe them into a text format by entering the text into a word processing or medical transcription software application using a keyboard. Electronic speech recognition software may also automatically detect the clinician's spoken words or acronyms and transcribe them into a text format. A medical transcriptionist may still need to review the transcription to correct spelling, formatting, interpretive errors, or abbreviations that may introduce dangers if incorrectly transcribed as identified by a regulatory agency, or expand an acronym to its full word or phrase.

Medical transcriptionists and medical personnel using other medical applications may need to produce a very high quality and accurate work product while meeting completion deadlines. Often, they perform a significant amount of research to meet quality standards before the clinician will approve the work product. For example, medical personnel may need to consult medical dictionaries, online resources, or other reference material to determine an accurate spelling of a word or other information, such as another physician's complete contact information. Such reference material may include electronic and paper-based tools, such as word lists, medical dictionaries, and drug references. At least some of the reference materials, however, may not be up-to-date in view of the rapid and robust pace at which vocabularies and information changes in the medical field. Use of such reference materials may result in a work product that contains inaccurate, incomplete, or otherwise lower quality terminology. The effect of such work product could result in incorrect diagnosis or treatment, leading to less than adequate patient care. Such inadequate care can result in physical harm or even death to the patient.

Accordingly, a need exists for systems and methods that provide medical application users with access to up-to-date medical information that includes reference material. Furthermore, a need exists for systems and methods that provide medical application users with access to reference material in a timely manner.

SUMMARY

Systems and methods according to some embodiments of the present invention provide a medical application with access to medical information. Attributes of a data source are received. The attributes are scored to generate a ranking of the data source. The data source is determined to be a medical information expert based on the ranking. Medical information is received from the data source that is, or otherwise associated with, the medical information expert. The medical information is stored in a knowledge database. A medical information request is received from the medical application. The knowledge database is searched based on the medical information request to generate a response to the medical information request. The response includes at least part of the medical information. The response is returned to the medical application in a format adapted to be customized by the medical application.

In some embodiments, the attributes include an identification attribute, a certification attribute, a historical information attribute, a medical information type attribute, and/or a volume attribute.

BRIEF DESCRIPTION OF THE DRAWINGS

These and other features, aspects, and advantages of the present invention are better understood when the following Detailed Description is read with reference to the accompanying drawings, wherein:

FIG. 4B is a screen shot of a medical terminology search tool for medical reference publications provided from a knowledge database according to one embodiment of the present invention;

FIG. 5A is a screen shot of a search tool for styles of medical terms from a knowledge database according to one embodiment of the present invention;

FIG. 5B is a screen shot of a search tool for styles of medical terms providing examples using medical information provided from a knowledge database according to one embodiment of the present invention;

FIG. 6A is a screen shot of normal lab values tool using medical information from a knowledge database according to one embodiment of the present invention;

FIG. 6B is a screen shot of results from a normal lab values tool using medical information provided from the knowledge database according to one embodiment of the present invention;

FIG. 7 is a screen shot of a physician's contact information tool using contact information provided from a knowledge database according to one embodiment of the present invention; and FIG. 8 is a screen shot of a spell check tool using medical information provided from a knowledge database according to one embodiment of the present invention.

DETAILED DESCRIPTION

Systems and methods according to various embodiments of the present invention provide medical information from a knowledge database to a medical application. The knowledge database can include medical information from data sources associated with verified and "trusted" medical information experts. In some embodiments, the knowledge database includes medical information from medical information experts that have been validated using pre-set criteria. For example, attributes of a purported medical information expert can be received. The attributes can be scored using pre-set criteria. A ranking can be generated from the scored attributes and compared to a pre-set threshold. If the ranking exceeds the pre-set threshold, the purported medical information expert is identified as a medical information expert and its medical information is received and stored in the knowledge database. In some embodiments, the medical information is continuously updated to provide up-to-date and accurate medical information to medical applications.

A medical information request from a medical application can be received. The medical information from medical information experts in the knowledge database can be searched based on the medical information request. Search results that include medical information in response to the request can be provided to the medical application. The medical information may be useful to medical personnel and in a format that the medical application can customize to its needs and requirements.

Illustrative Medical Information Access System

Figure 1:
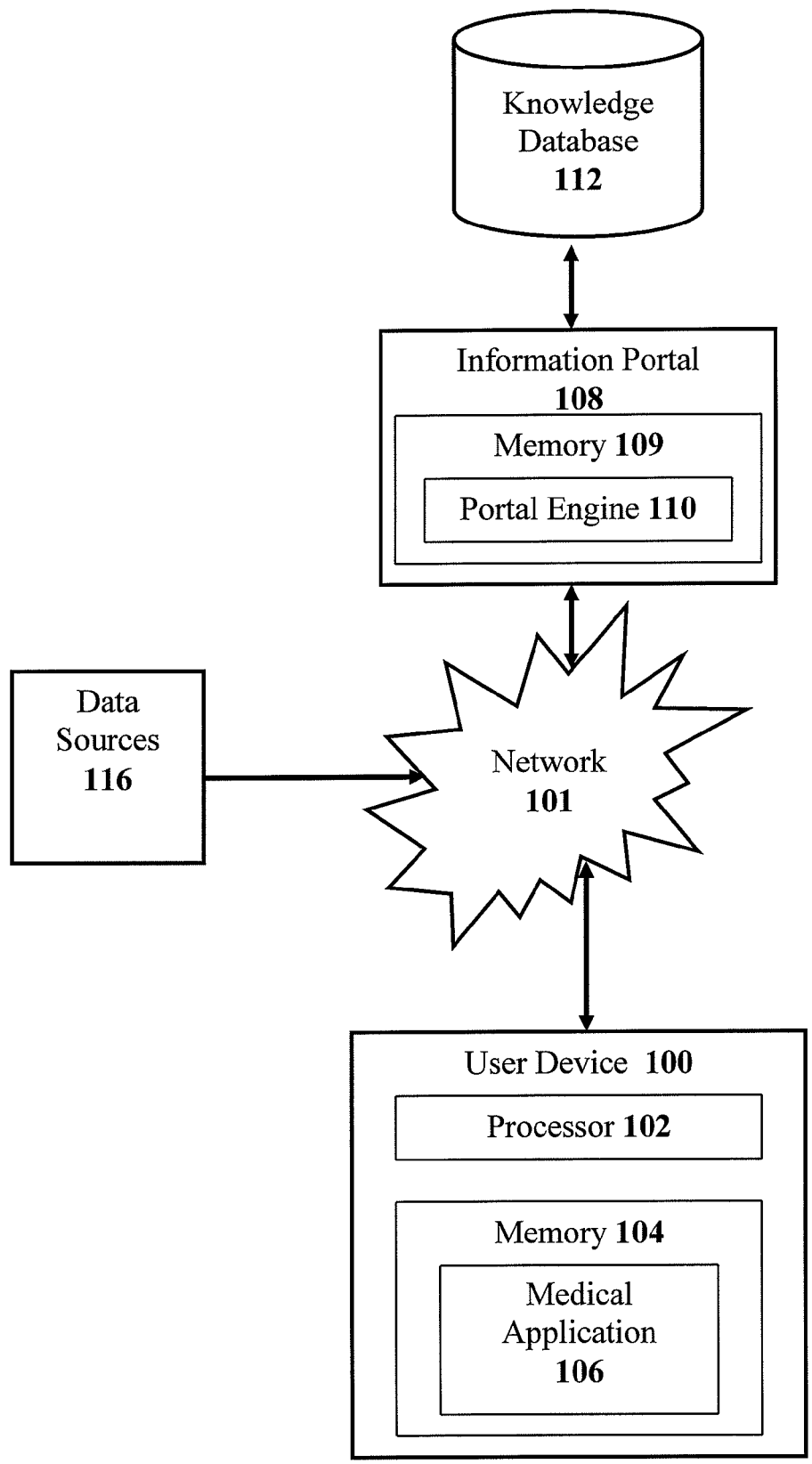
FIG. 1 is a block diagram of a knowledge database and information portal system in communication with a medical application according to one embodiment of the present invention.

FIG. 1 illustrates one embodiment of a system for validating medical information experts, storing medical information from medical information experts, and providing medical information to a medical application. An information portal 108 is shown in communication with a user device 100 and one or more data sources 116 through a network 101. The information portal 108 may also be in communication with a knowledge database 112. The information portal 108 is configured to receive medical information from the one or more data sources 116, store the medical information in the knowledge database 112, and provide the user device 100 with access to the medical information.

In some embodiments, the information portal 108 is a processor-based device that includes a computer-readable medium, such as memory 109. The memory 109 is configured to store executable code such as a portal engine 110. As described in more detail below, the portal engine 110 may be configured to perform data source validation, store data in the knowledge database 112, provide web page services and/or provide data from the knowledge database 112 to the medical application over the network 101. The portal engine 110 may one or more software applications. In addition, the one or more software applications may be located on one or more devices that are collectively the information portal 108. Examples of the information portal 108 include a server and computer. The network 101 may be any type of data network, examples of which include the Internet, wide area network (WAN), local area network (LAN), or a combination of these and other type of networks.

The user device 100 may include a processor 102 and a computer-readable medium such as memory 104. A medical application 106 may be stored in memory 104 and adapted to be executed by the processor 102. The user device 100 may be adapted to be used by medical personnel to access the medical application 106 and perform medical information-related tasks. The medical application 106 may be configured, manually or automatically, to submit a request for medical information over the network 101 to the information portal 108. The user device 100 can also include an input device (not shown) to receive inputs or other commands from a user and an output device (not shown) to provide information, such as on a user interface, to a user.

The one or more data sources 116 may each be associated with a purported medical information expert, such as a medical information provider, that may be capable of providing trusted medical information. As described in more detail below, the portal engine 110 may be capable of determining if the one or more data sources 116 is associated with a medical information expert based on attributes of the medical information expert and, if so, receiving medical information from the one or more data sources 116. The one or more data sources 116 can include a database, server, or other device capable of sending data to the information portal 108.

The knowledge database 112 may be a searchable database that includes medical information stored on a computer-readable medium. Examples of knowledge databases 112 include a flat file database, relational database, and a redundant array of independent disk (RAID). In the embodiment illustrated in FIG. 1, the information portal 108 is connected directly to knowledge database 112. The knowledge database 112 may also be connected to the information portal 108 over a network such as the Internet, a local area network (LAN) or a wide area network (WAN). In some embodiments, the knowledge database 112 is associated with a server or other processor-based device through which it can communicate with the information portal 108. In other embodiments, the information portal 108 can include the knowledge database 112. The knowledge database 112 can contain a variety of medical information or other information that is indexed in a searchable format. The knowledge database 112 may be configured to continuously receive updates to the medical information from the one or more data sources 116 through the network 101 and information portal 108.

In some embodiments, the knowledge database 112 includes a knowledgebase web farm and a knowledgebase service cluster. The knowledgebase web farm may include web servers that can host content, such as medical information that is indexed. The knowledgebase service cluster may include database servers hosting different aspects of the knowledge database 112. For example, one database server may include physician lookup, and a separate database server may include medical definitions. The knowledgebase web farm and knowledgebase service cluster may be connected by a network link. The network link can be the Internet, LAN, and/or WAN, or a combination of these and other type of networks. In some embodiments, the medical application 106 identifies the type of medical information it seeks or otherwise limits its request to particular medical information. The portal engine 110 can use the identification to limit its search or the medical application's 106 access to certain medical information or databases.

In some embodiments, the medical information from the knowledge database 112 can be used by the medical application 106 as a resource to determine information needed, to confirm correct information, or otherwise to use the information as updated and correct information in a medical-related task. For example, the medical application 106 may be a transcription application used by medical personnel to transcribe notes generated by a medical provider. The medical information can be used by the medical application 106 to confirm a spelling of a medical term, confirm the correct address for a medical provider, and/or determine the medical term associated with an acronym in the medical provider's notes. The information portal 108 can be configured to provide requested medical information to the medical application 106 over the network 101 and in a format that can be customized by the medical application 106 for its particular needs and purposes.

Illustrative Medical Information Access Method

Figure 2:
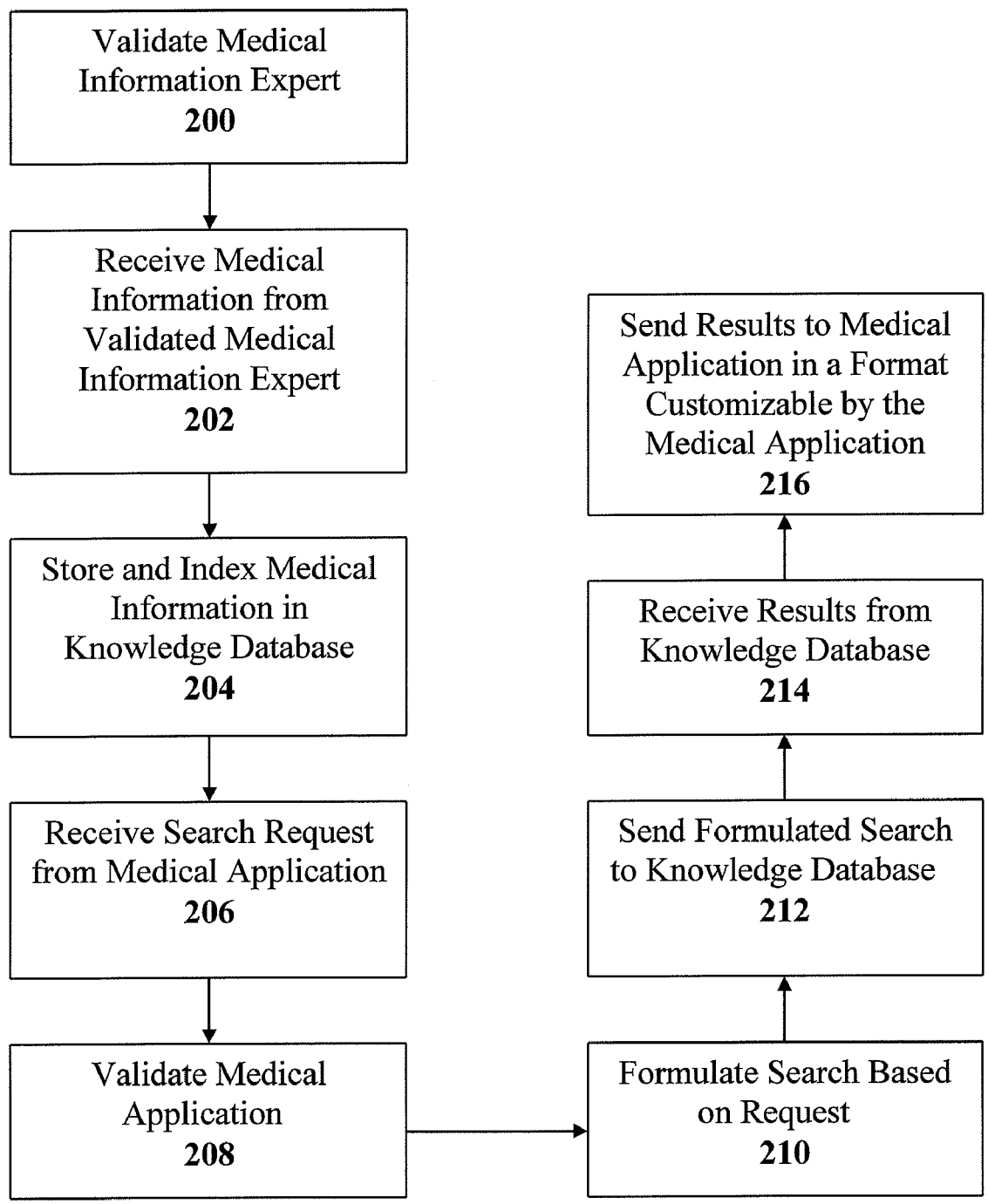
FIG. 2 is a flow diagram of a process for providing information from a medical information expert to a knowledge database and providing access for a medical application to the medical information according to one embodiment of the present invention.

Various methods according to various embodiments of the present invention can be used to determine if a data source is a medical information expert and provide a medical application with access to medical information from the medical information expert. FIG. 2 is flow diagram of one embodiment of a method for validating data sources and providing access to information from validated data sources. For purposes of illustration only, the elements of this method are described with reference to the system depicted in FIG. 1 and the flow chart depicted in FIG. 3. Other implementations are also possible.

The method may begin at block 200 when the portal engine 110 validates a medical information expert. In some embodiments, the portal engine 110 validates a medical information expert based on attributes received from a data source 116 associated with a purported medical information expert. For example, the portal engine 110 may receive a request to provide medical information from a data source 116 that includes attributes of the purported medical information expert associated with the data source 116. In some embodiments, the portal engine 110 periodically submits requests to potential medical information experts for them to submit attributes that can be scored. In other embodiments, the medical information expert provides the request to the portal engine 110.

The portal engine 110 can use any method to determine if the data source 116 is associated with a medical information expert based on attributes. In one embodiment, the attribute is a certification attribute in which the purported medical information expert is certified by a third-party, such as the Association for Healthcare Documentation Integrity (AHDI). A score of the certification attribute with the credentials from the third-party may be positive, or other indicator that the purported medical information expert is a "trusted' source, and the purported medical information expert is identified as a medical information expert. Medical information is received from it thereafter. Other methods may be used that include validation based on a certification attribute. Some methods use other types of attributes to validate.

Figure 3:
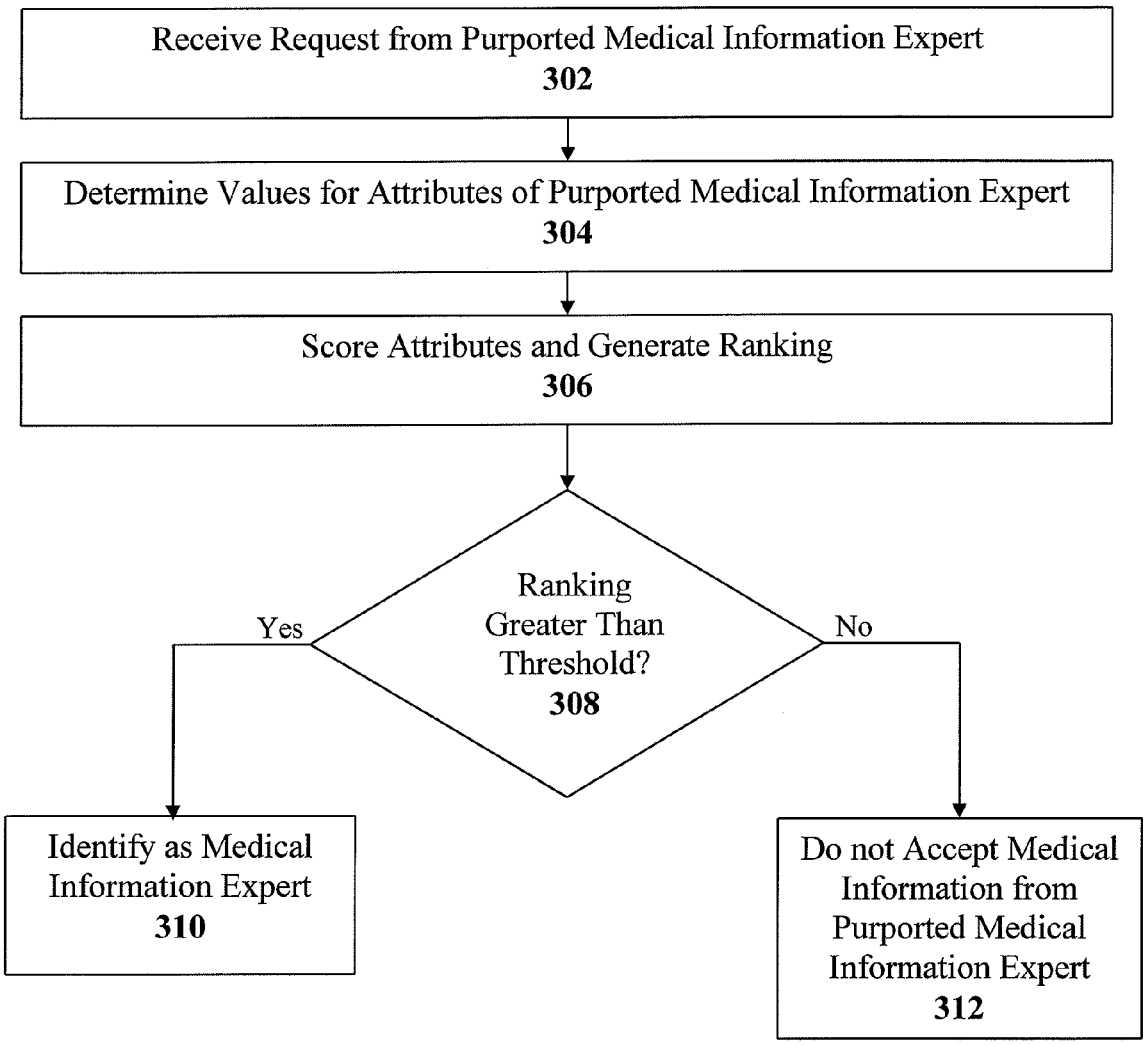
FIG. 3 is a flow diagram of a process for validating a medical information expert according to one embodiment of the present invention.

FIG. 3 illustrates one method for validating a medical information expert. The exemplary medical information expert validation method begins at block 302 when the portal engine 110 receives a request from a data source 116 for consideration as a medical information expert and to be a medical information provider. The request can include one or more attributes associated with data source 116. Examples of attributes include data source identification, history, certification(s), the type of medical information the data source 116 can provide, and the amount of medical information the data source 116 can provide. In some embodiments, the portal engine 110 requires certain attributes to be received from the data source 116 before a validation process is performed. In other embodiments, the portal engine 110 receives any attributes the data source 116 can provide and validates the data source 116 based on the received attributes.

In block 304, the portal engine 110 determines attribute values for each attribute received from the data source 116. In some embodiments, the portal engine 110 can analyze the attributes and identify the specific value associated with each attribute. For example, an identification attribute can include a name of the purported medical information expert associated with data source 116. A history attribute can include historical information on the purported medical information expert's past activities in providing medical information. Examples of historical information include the entities to which the data source 116 has provided medical information, the amount of time the data source 116 has provided medical information, and reasons, if any, why the data source 116 no longer provides medical information to certain entities. A certification attribute can identify the industry or governmental groups, such as AHDI, that certify the data source 116. An affiliation attribute can identify the industry or governmental groups to which the data source 116 is a member. A type of medical information attribute can identify the category of medical information the data source 116 can provide. An amount of medical information attribute can identify the number of medical information data elements the data source can provide. Other attributes may be implemented in some embodiments of the present invention.

In block 306, the portal engine 110 scores each attribute to generate a ranking for the data source 116. Attributes can be scored based on the value of each attribute. In some embodiments the ranking is a composite of the score for each attribute. In other embodiments, the ranking includes a ranking for each attribute. One attribute may be scored and ranked or more than one attribute may be scored and ranked. The portal engine 110 can score each attribute using the same or different methods. In some embodiments, the portal engine 110 scores an attribute by comparing the attribute value to a table of information identifying standard values and a score for each value. The portal engine 110 can look the attribute value up in the table by matching the attribute value to the standard value and identifying the score associated with that standard value. The portal engine 110 may also identify a rank for the attribute value based on the score. In some embodiments, the table of information includes a rank associated with each standard value.

For example, the portal engine 110 can use the value of an identification attribute to look the purported medical information expert up in a table that includes standard values of the identification attribute stored in memory 109. The table can include an identification of medical information experts and a score or rank for each of the medical information expert listed in the table. If the portal engine 110 locates the purported medical information expert in the table, it can assign the score or rank associated with the purported medical information expert. The score or rank for each medical information expert in a table may be generated by the portal engine 110 based on criteria provided to the portal engine 110 or the score or rank may be received from another source.

The table may include a list of any purported or potential medical information experts. For example, the United States Food and Drug Administration (FDA) is a government agency administered by the United States Department of Health and Human Services and may be one medical information expert listed in the table. The FDA is responsible for protecting the public health by assuring the safety, efficacy, and security of human and veterinary drugs. Medical information generated by the FDA is often subject to a high level of scientific and research standards. Based on such criteria, the FDA or similar medical information expert may be scored relatively high as a "trusted" source of medical information.

Private organizations and research institutions may also publish information for healthcare research. Some publications experience a relatively high level of peer review or other metrics that analyze the accuracy or other factors associated with the information. Some publications do not provide for a relatively high level or review and analysis. Some of the private organizations can be included in the table and associated with a score that reflects the amount of review and analysis performed on the information generated by the private organization. In some embodiments, scores range from one to ten or from one to one hundred, where a score of one reflects a highly ranked medical information expert and a score of ten or one hundred reflects a low ranked medical information expert.

Other attributes may be scored on the same or different scale and using the same or different methods. For attributes scored on a different scale, the portal engine 110 may be configured to normalize the scores before generating a composite rank for the purported medical information expert. Examples of scoring other attributes include the following:

- A certification attribute may be scored by comparing the associations certifying a purported medical information expert with a list of certification associations. The certification associations may be associated with a score or rank based on their reputation in the medical information community, the amount of time they have been in existence or other criteria indicating the trustworthiness and ability of the certification association.
- A historical information attribute may be scored using a sliding scale. For example a purported medical information expert that has been providing medical information for a long period of time may be ranked higher than a purported medical information expert that has been providing medical information for a shorter period of time. Other factors, such as to whom the purported medical information expert has provided data in the past may be scored using a sliding scale.
- A medical information type attribute can also be scored. The medical information type attribute can be determined by the type of medical information available from the data source. For example, one type of medical information may be addresses of physicians within a geographical area and a second type of medical information may be medical terms associated with heart-related diseases. Scoring the medical information type attribute may be based on whether the knowledge database 112 needs the type of medical information or if the knowledge database 112 needs to receive the type of medical information faster than it is currently receiving from another medical information expert.
- A volume attribute can also be scored by a sliding scale. The volume attribute may be the quantity of medical information the data source can provide. The volume attribute can be scored based on the amount of medical information offered by a data source. For example, purported medical information experts (data sources) that can provide a relatively large amount of medical information may be scored higher than those than can provide a relatively small amount of medical information.

Once attributes of a purported medical information expert have been scored, a ranking is generated by the portal engine. The ranking may be a composite ranking of all the scored attributes. For example, the ranking may be an average ranking for the scored attributes. In some embodiments, attributes may be weighted higher or lower such that scores for some attributes effect the composite ranking more.

After the ranking is generated based on the score, the portal engine 110 determines if the ranking exceeds a pre-set threshold in block 308. In some embodiments, the pre-set threshold is determined based on survey statistics and standard data on existing medical information experts and the attributes associated with them. The pre-set threshold may be any number, rank, or other scoring scale associated with the scale of the composite ranking. For example, the pre-set threshold may be four for a ranking scale of one to ten, in which one represents a highly ranked purported medical information expert and a rank of ten represents a low ranked purported medical information expert. Rankings of one to three are higher than the pre-set threshold of four, while rankings from four to ten are not higher.

The process of ranking based on one or more attributes and comparing a composite rank to a pre-set threshold allows a purported medical information expert to be validated as a medical information expert even if they do not score highly for some attributes, but score highly in others. For example, a relatively unknown purported medical information provider may not score high on the identification attribute or history information attribute, but score high for the certification attribute and type of medical information attribute. In some embodiments, a ranking for each attribute is compared to a pre-set threshold to determine if a certain number of attributes exceed the threshold.

If the ranking is greater than the pre-set threshold (e.g. the ranking is higher ranked than four in the example above or a certain number of attributes rank higher than a pre-set threshold), the portal engine 110 identifies the purported medical information expert as a medical information expert in block 310. For example, the portal engine 110 may certify that the purported medical information expert is an entity from which the portal engine 110 will accept data and provide the medical information expert with a passcode, electronic key, or other identifiable file (electronic or otherwise) to prepare to receive medical information from the medical information expert. In some embodiments, the pre-set threshold is one hundred percent or another value that requires the attributes of the purported medical information expert to meet standards previously established in the portal engine 110 before it is considered as a "trusted" source.

If the ranking is less than the pre-set threshold, the portal engine 110 may refuse to accept medical information from the purported medical information expert in block 312.

Returning to FIG. 2, after a medical information expert associated with a data source 116 is validated, the portal engine 110 can receive medical information from the validated medical information expert in block 202. In some embodiments, the portal engine 110 receives a passcode, electronic key or similar identification that the medical information expert has been validated each time it receives medical information from the medical information expert. Examples of medical information include physician name and address, correct spelling of medical terms, definitions of medical-related acronyms, and ranges for medical parameters. For example, the medical information can include a realistic range for a medical parameter such as blood pressure. The realistic range can be used by a medical application to determine if a transcribed note, for example, falls outside the realistic range, indicating the note was likely transcribed incorrectly.

The medical information can include data elements. Each data element includes specific medical-related information. The data elements can also relate to each other. For example, a group of data elements may include specific medical-related information associated with one topic. The medical information may be continuously received by the portal engine 110 from the medical information expert. In some embodiments, the portal engine 110 is configured to periodically request medical information from the medical information expert.

In block 204, the portal engine 110 stores and indexes the medical information in the knowledge database 112. For example, the portal engine 110 may index the medical information based on the topic to which it relates and/or topics of medical information already stored in the knowledge database 112. In other embodiments, the portal engine 110 indexes the medical information based on the source of the information, such as by medical information expert. Instead of indexing and storing the medical information, some embodiments of the portal engine 110 send the medical information to the knowledge database 112 and the knowledge database 112 is configured to index and store the medical information.

In block 206, the portal engine 110 receives a search request for medical information from the medical application 106. The search request may include any type of request for medical-related information that may be stored in the knowledge database 112. Examples of search requests include a physician name and/or address lookup, spell-check, and parameter range lookup. In some embodiments, the request may include the parameters of the search. In other embodiments, the request includes values to be searched, but not search parameters. The portal engine 110 may require the medical application 106 to provide credentials along with its request. The credentials can include a username, passcode, unique identifier, and/or any other identifier such as those used in subscription-based services. In some embodiments, the portal engine 110 does not require credentials from the medical application 106 before access to its services is provided.

In block 208, the portal engine 110 may validate the medical application 106 to determine if it can access the knowledge database 112. In some embodiments, the portal engine 110 services medical applications that have subscribed to services provided by the portal engine 110. The portal engine 110 may receive medical application credentials, such as username, password, or other account credentials, and determine if the medical application is a subscriber to the service. In other embodiments, the portal engine 110 does not validate the medical application 106 and, instead, provides access to the medical application 106 if the portal engine 110 receives an appropriate request for information.

In block 210, the portal engine 110 formulates a search for medical information in the knowledge database 112 based on the request from the medical application 106. In some embodiments, the portal engine 110 passes the request to the knowledge database. In other embodiments, the portal engine 110 formulates search parameters based on the specific information in the request. For example, the portal engine 110 may formulate search parameters that correspond to the indexing system in the knowledge database 112 and based on the subject of the request from the medical application 106.

In block 212, the portal engine 110 sends the formulated search to the knowledge database 112. In some embodiments, the portal engine 110 conducts the search on the knowledge database 112 by accessing the medical information stored in the knowledge database 112 and identifying medical information responsive to the search parameters. In other embodiments, the portal engine 110 provides the formulated search to the knowledge database 112 where the knowledge database 112 performs the search on its contents. Search algorithms, such as least-edit or phonetic matching algorithms, may be used in some embodiments to provide results relevant to the search parameters.

In block 214, information responsive to the formulated search is received by the portal engine 110. The information may include one or more data elements in which information relevant to the formulated search parameters are stored. The responsive information may be received in any format. An example of a format includes an extensible markup language (XML) format. In some embodiments, the portal engine 110 processes the responsive information to further refine or otherwise remove certain information if it is not particularly relevant to the request from the medical application 106.

In block 216, the portal engine 110 provides the results to the medical application 106 in a format that is adapted to be customized by the medical application 106. For example, the results may be in a format in which the medical application 106 can customize its presentation or use for a user. Examples of formats that are adapted to be customized by the medical application 106 include XML, hypertext markup language (HTML) and representational state transfer (REST). Examples of customized presentations include data that is selectable by a user, automatically inserting results in an electronic document or file, and ordering the search results in a preferred method.

Any type of medical information can be stored in knowledge database 112 and provided to medical application 106. Examples of medical information include normal ranges for treatment protocols and colloquialisms. Normal ranges may be the normal range of a characteristic typically measured during a treatment protocol, such as a cancer protocol. The normal range may be a range in which measured values of the characteristic could potentially fall. Values outside the normal range may indicate nonsensical values that may be erroneous. Colloquialisms may include slang or other saying particular to a dialect of a language or other sub-language group. They can be helpful, for example, when a medical transcriptionist is not familiar with the slang used in notes or other documentation they are transcribing, but need to determine the correct word and spelling used.

In some embodiments, the information portal 108 may include, or connected to, a web server. The portal engine 110 may be configured to generate a web page on which responses can be provided to users. For example, the portal engine 110 can include a medical services application that is web-based and provided to a user's computer or other device over a network such as the Internet or an intranet. The medical services application may be any application in which medical information can be entered, formatted, and/or processed. Examples of medical services application can include a medical transcription application, electronic health record system, medical coding, medical billing system, and speech recognition systems. The medical services application can be used by medical personnel to enter and organize information over the network. In some embodiments, the work created by the medical personnel using the medical services application can be saved on the information portal or another location on the network. In other embodiments, the work created can be stored on the user's device.

The portal engine 110 can be configured to provide the medical services application with access to medical information from medical information experts that is stored in the knowledge database 112. Instead of providing a response to a request for medical information in a format that can be customized by a medical application, the portal engine 110 can generate a web page that includes the response and/or integrate the response with the work being created by the user. For example, the medical services application may be used to enter notes from a patient's visit in which the medical provider suggested that the patient see a specialist. The medical services application can submit a request for the correct spelling of the specialist's name and his or her office address. A response can be returned and automatically inserted in an appropriate area in the work being created by the medical personnel. Another example, may be a medical transcription application in which the portal engine 110 is configured to automatically identify suspect words, such as those that may be spelled incorrectly or have different meanings depending on the context of their use. In some embodiments, the portal engine 110 can automatically provide information from the knowledge database 112 regarding the suspect words.

Illustrative Examples of Access to Medical Information from Medical Information Experts The following describes examples of using certain specific embodiments of the present invention to provide a medical application with access to medical information from medical information experts. The examples are described with reference to FIGS. 4 through 8, which illustrate graphical user interfaces generated by a medical application that is a medical transcription application. However, other types of medical applications can be used with various embodiments of the present invention and various user interfaces can be provided by such medical applications. Medical transcription often involves converting spoken or hand written words of a clinician into a text format in electronic form. The transcriptionist often consults medical dictionaries, online resources, or other reference material to determine an accurate spelling of a word, definition of an abbreviation, an acceptable range for a clinical result, a physician's contact information, and/or other information. In an exemplary embodiment, the transcriptionist interacts with a medical transcription software application at a work station.

Medical information experts are validated and medical information from medical information experts is received and stored in a knowledge database. The medical information experts are validated by receiving attributes of the medical information experts and scoring the attributes to determine that the medical information expert meets criteria of a "trusted" data source.

The medical transcription application can access the medical information through an information portal. The information portal provides requested medical information to the medical transcription application in an XML format that the medical transcription application can customize and display all or part of the returned medical information to a user on a graphical user interface. The workstation and medical transcription application communicate via the Internet with the information portal to receive medical information. The description of FIGS. 4-8 below provide examples that illustrate uses of medical information from validated medical information experts by a medical transcription application.

The medical transcription application illustrated in FIGS. 4 through 8 connects to the Internet and enters a validation process through a portal engine. The portal engine is an application executing on an information portal that is a server, such as a web server, connected to the Internet and associated with an Internet address such as a Uniform Resource Locator (URL). The portal engine services the medical transcription application by providing access to a knowledge database containing medical information from one or more validated medical information experts. The medical information can include medical reference publications on various medical topics, physician names and address, and/or medical dictionaries.

Figure 4A:
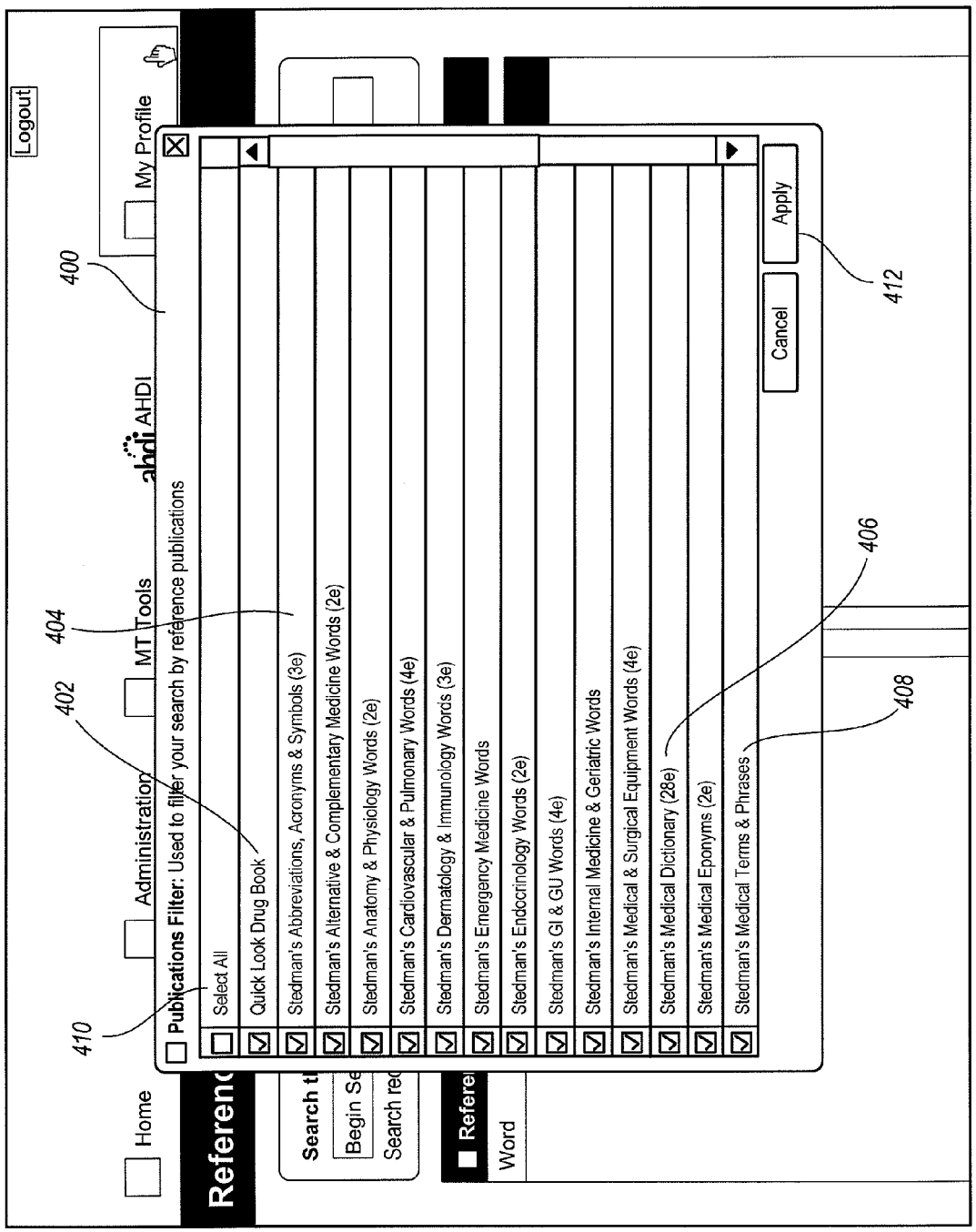
FIG. 4A is a screen shot of a medical reference publication selection menu with medical information provided from a knowledge database according to one embodiment of the present invention.

A medical transcriptionist logs into the medical transcription application and selects one or more medical reference publications from which to search as illustrated in FIG. 4A. These medical reference publications may be stored in the medical knowledge database. The medical transcription application can access these medical reference publications in the medical knowledge database through the portal engine. The medical transcription application receives information about these reference publications from the medical knowledge database and customizes the results to present the medical transcriptionist with a list of reference publications form which to choose. In the example illustrated in FIG. 4A, the medical transcriptionist is presented with a dialog box 400 offering choices including a number of "Stedman's" publications and/or the "Quick Look Drug Book." The medical transcriptionist may select one or more of the medical reference publications from which to search. The examples below may include search results from the selected "Quick Look Drug Book" 402, "Stedman's Abbreviations, Acronyms & Symbols (3e)" 404, "Stedman's Medical Dictionary (28e)" 406, and "Stedman's Medical Terms and Phrases" 408, for example. Alternatively, all of the reference publications can be selected 410 for search. Once the medical reference publications are selected, the transcriptionist may select the "Apply" button 412 and begin transcribing a medical document.

FIG. 4B illustrates further examples of how the medical transcription application may use the medical knowledge database services that are provided by the information portal engine. In this example, the medical transcriptionist needs to lookup an abbreviation or acronym beginning with the letters "mers" using a reference tool 414. The dialog box 418 allows the transcriptionist to enter the terms to be searched. The transcriptionist enters the first four characters "mers" and a wild-card term "%" or "mers %" which tells the medical transcription application to ask the portal engine to search the selected medical reference publication in the medical knowledge database for all terms beginning with "mers." The medical transcriptionist has previously selected the medical reference publication "Stedman's Abbreviations, Acronyms & Symbols (3e)" 416 to search. For example, the medical application may subscribe to certain databases or types of information from which the medical transcriptionist can select to search. The portal engine searches the "Stedman's Abbreviations, Acronyms & Symbols (3e)" 416 publication for any terms beginning with "mers." The results of the search are returned by the portal engine to the medical transcription application in a format that can be customized by the medical transcription application. The medical transcription application presents the customized results as a list of references in block 420.

FIGS. 5A and 5B illustrate another example of a medical transcription application using information provided from the knowledge database. FIG. 5A illustrates the medical transcription application accessing the Association for Healthcare Documentation Integrity (AHDI) book of style medical reference. The medical transcriptionist selects the AHDI icon 508, which prompts the medical transcription application to access information stored in the knowledge database for this reference. Specifically, the selection in this example allows the medical transcription application to access the "AHDI Book of Style" reference database within the medical knowledge database. The medical transcription application can maintain continuous and constant contact with the medical knowledge database via the portal engine. As the medical transcriptionist enters characters in the dialog box 500, the AHDI reference database 112 is searched for terms starting with the characters entered up to that moment in time. A corresponding drop down dialog box 502 appears with list of medical terms related to the search. The medical transcriptionist can continue to enter the terms or scroll down the list and select the terms of interest. In this example, the medical transcriptionist is interested in the proper manner of indicating "temperature" and "temperature scales." These terms are selected for lookup in the dialog box 500. The portal engine searches the AHDI reference in the medical knowledge database for methods of expressing these terms. The portal engine returns the search results to the medical transcription application. The results of the search are presented by the medical transcription application as a list of examples 506, as shown in FIG. 5B.

Other examples of the type of information that can be accessed from the knowledge database are shown in FIGS. 6A and 6B. For example, selecting the AHDI icon in this example allows the medical transcription application to access the "AHDI Normal Lab Values" reference database within the medical knowledge database. Here the medical transcriptionist selects a "Category" icon 602 which present a dialog box 604 with a list of categories. The medical transcriptionist selects the Cardiopulmonary Lab 606 category as shown in FIG. 6B. Again, the medical transcription application contacts the information portal engine to access the medical knowledge database. The information portal engine searches the "AHDI Normal Lab Values" reference database within the medical knowledge database. The results of the search are formatted by the information portal engine to be customized by the medical transcription application. As shown in FIG. 6B the results are presented in a list of "Items" 608 and "Normal Values" 610. This information would allow a medical transcriptionist to verify information they are translating into electronic text form is within "normal" range of values. In this example, the normal range of values for a "Cardiac Index" is "2.5-4.2 L/min/m2." If the medical transcriptionist reads a handwritten note from a medical doctor in which the doctor wrote "a patient has a normal 'Cardiac Index'" and the medical transcriptionist understood from the notes that the patient's Cardiac index is between 25.0 or 2.5 L/min/m2, the transcriptionist could ascertain the index more likely is 2.5 L/min/m2, because 25.0 L/min/m2 would have been significantly outside the normal range.

Figure 8:
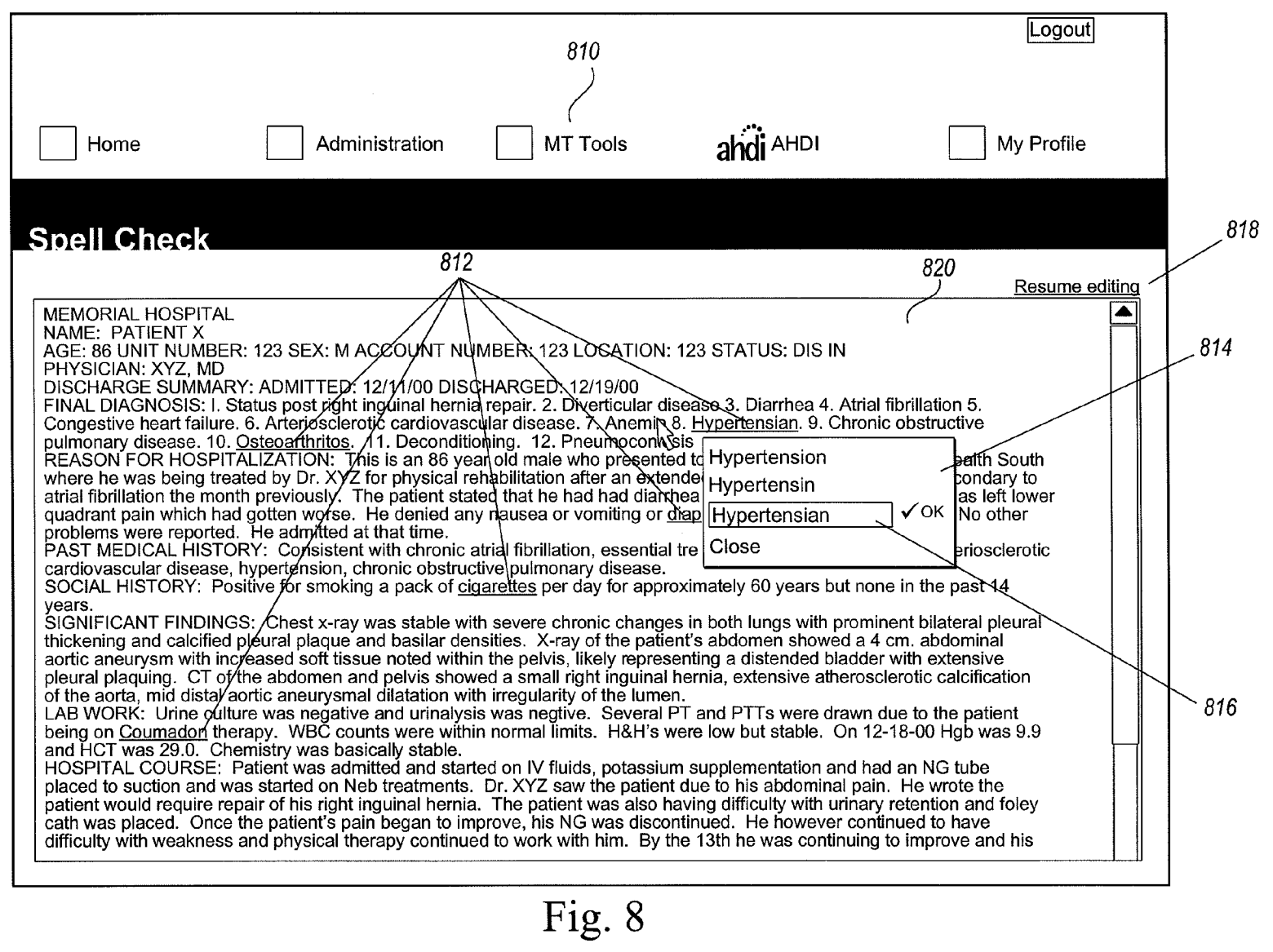

In still another embodiment, illustrated by FIGS. 7 and 8, other types of information can also be searched in the medical knowledge database. FIG. 7 illustrates a contact information tool that allows a user or the medical transcriptionist to look up contact information for a health care provider. In this example, the medical transcriptionist uses a physician look up tool 700 in the medical transcription application. A dialog box 702 allows the medical transcriptionist to enter such information as first, last name, medical specialty, city, state, and zip code. In this example, the medical transcriptionist enters the letters "jo" in both the first and last name fields of the dialog box 702. Again, the medical transcription application requests the services of the information portal engine to search a contact information database within the medical knowledge database for contact information about a particular physician. The results of the search are formatted by the information portal engine to be customized by the medical transcription application. These results appear in a list of physician contacts 704. If the medical transcriptionist selects a particular physician's name, for example, in this case "John R. Johansson" 706, a pop-up dialog box 708 appears with more detailed contact information about the physician.

FIG. 8 illustrates an example of how the medical knowledge database may be used for spell checking. For example, the document 820 in FIG. 8 is an example of a transcribed medical document entered by a medical transcriptionist. In an exemplary embodiment, the transcribed medical document 820 may be checked for spelling errors either while text is being entered or on demand by selecting the "MT Tools" icon 810. In an exemplary embodiment, the medical transcription application is connected to the information portal engine and subscribes to the medical knowledge database in a consistent and ongoing fashion. As the medical transcriptionist enters text, information portal engine allows the medical knowledge database to be searched in real-time via the network connected to the user's device. In alternative embodiment, the information portal engine downloads a medical dictionary from the medical knowledge database to the user's device. The downloaded medical dictionary can be searched locally on the user's device. As illustrated in FIG. 8, misspelled words 812 are highlighted and underlined throughout the document. Once a misspelled word 812 is selected, a dialog box 814 appears with alternate spellings of the highlighted word. The medical transcriptionist is a able to select the correct spelling of the word 816 and continue editing. Once the medical transcriptionist has finished spell checking the document, the transcriptionist can leave the spell check tool by selecting the "Resume editing" function 818.

These and other embodiment and features of the medical transcription application are designed to take advantage of the information stored in the medical knowledge database and the processes managed by the information portal engine. These features are also designed to improve the accuracy of the medical information contained in a patient's health care record.

GENERAL

The foregoing description of the embodiments, including preferred embodiments, of the invention has been presented only for the purpose of illustration and description and is not intended to be exhaustive or to limit the invention to the precise forms disclosed. Numerous modifications, adaptations, and uses thereof will be apparent to those skilled in the art without departing from the spirit and scope of this invention.

What is claimed is:

1. A method for providing a medical application with access to medical information, the method comprising:
    receiving at least one attribute of a data source;
    scoring the at least one attribute to generate a ranking of the data source;
    determining the data source is a medical information expert based on the ranking;
    receiving medical information from the data source;
    storing the medical information in a knowledge database;
    receiving a medical information request from the medical application;
    searching the knowledge database based on the information request to generate a response to the medical information request, the response comprising at least part of the medical information; and returning the response to the medical application in a format adapted to be customized by the medical application.

2. The method of claim 1, wherein the at least one attribute is an identification attribute or a certification attribute, the identification attribute identifying the data source, the certification attribute identifying at least one association certifying the data source; and wherein scoring the at least one attribute to generate a ranking of the data source comprises:
determining a value for the at least one attribute;
matching the value on a table of attribute values; and
determining a score for the at least one attribute from the table.

3. The method of claim 1, wherein the at least one attribute is a historical information attribute or a volume attribute, the historical information attribute comprising a value associated with a history of the data source providing medical information, the volume attribute comprising a value for an amount of medical information the data source can provide; and wherein scoring the at least one attribute to generate a ranking of the data source comprises:
comparing the value to information on other providers; and
determining a score based on the comparison, wherein the score is a relative ranking of the data source.

4. The method of claim 1, wherein the at least attribute is a medical information type attribute comprising an identification of a type of medical information the data source can provide; and wherein scoring the at least one attribute to generate a ranking of the data source comprises determining a score based on the type of medical information the data source can provide.

5. The method of claim 1, wherein determining the data source is a medical information expert based on the ranking comprises:
comparing the ranking to a threshold; and
determining the ranking exceeds the threshold.

6. The method of claim 1, wherein the at least one attribute comprises a plurality of attributes,
wherein scoring the at least one attribute to generate a ranking of the data source comprises:
normalizing a score for each of the plurality of attributes;
generating a composite ranking based on attribute scores; and
wherein the composite ranking is the ranking of the data source.

7. The method of claim 1, wherein the medical application is a medical transcription application.

8. A system comprising:
a processor-based device comprising a portal engine stored on a computer-readable medium, the portal engine being configured to:
receive attributes of a data source, wherein at least one of the attributes is a certification attribute comprising an identification of at least one association certifying the data source;
score the certification attribute by:
comparing the identification of the at least one association to a table of attribute values, each of the attribute values being associated with a value score;
matching the identification of the at least one association to one of the attribute values; and
identifying the value score associated with the matching one of the attribute values as a score for the certification attribute;
generate a ranking based on the score;
comparing the ranking to a threshold to determine the data source is a medical information expert;
receive medical information from the data source; and
store the medical information in a knowledge database.

9. The system of claim 8, wherein the portal engine is configured to:
receive an information request from a medical application;
generate a response to the medical information request, the response comprising at least part of the medical information from the knowledge database; and
return the response to the medical application in a format adapted to be customized by the medical application.

10. The system of claim 9, wherein the portal engine is configured to generate the response to the medical information request by formulating a search of the medical information based on the information request using least-edit or phonetic matching algorithms.

11. The system of claim 9, wherein the medical application is a medical transcription application.

12. The system of claim 8, wherein the attributes comprise at least one of:
an identification attribute comprising an identification of the data source;
a historical information attribute comprising a history of the data source providing medical information;
a medical information type attribute comprising an identification of a type of medical information the data source can provide; or
a volume attribute comprising an identification of an amount of medical information the data source can provide.

13. The system of claim 12, wherein the ranking is a composite ranking generated by the portal engine based on scores of attributes.

14. The system of claim 13, wherein the portal engine generates the composite ranking by:
normalizing a score for each attribute; and
determining the composite ranking based on normalized scores.

15. A non-transitory computer-readable medium on which is program code, the non-transitory computer-readable medium comprising:
program code for receiving attributes of a data source, wherein at least one of the attributes is a certification attribute comprising an identification of at least one association certifying the data source;
program code for scoring the certification attribute comprising:
program code for comparing the identification of the at least one association to a table of attribute values, each of the attribute values being associated with a value score;
program code for matching the identification of the at least one association to one of the attribute values; and
program code for identifying the value score associated with the matching one of the attribute values as a score for the certification attribute;
program code for generating a ranking based on the score;
program code for comparing the ranking to a threshold to determine the data source is a medical information expert;
program code for receiving medical information from the data source;

program code for storing the medical information in a knowledge database;

program code receiving an information request from a medical application;

program code for generating a response to the medical information request, the response comprising at least part of the medical information from the knowledge database; and program code for returning the response to the medical application in a format adapted to be customized by the medical application.

16. The non-transitory computer-readable medium of claim 15, wherein the format is an Extensible Markup Language (XML) format.

17. The non-transitory computer-readable medium of claim 15, further comprising:

program code for scoring the attributes;

program code for generating a composite ranking based on attribute scores, wherein the composite ranking is the ranking for the data source.

18. The non-transitory computer-readable medium of claim 15, wherein program code for generating the response to the medical information request:

program code for formulating the search based on the information request using least-edit or phonetic matching algorithms; and program code for receiving results from the knowledge database based on the search.

19. The non-transitory computer-readable medium of claim 18, wherein program code for generating the response to the medical information request comprises:

program code for formatting the results to generate the response.

20. The non-transitory computer-readable medium of claim 15, wherein the attributes comprise at least one of:

an identification attribute comprising an identification of the data source;

a historical information attribute comprising a history of the data source providing medical information;

a medical information type attribute comprising an identification of a type of medical information the data source can provide; or a volume attribute comprising an identification of an amount of medical information the data source can provide.

* * * * *